(12) United States Patent
Kumagai

(10) Patent No.: US 9,389,152 B2
(45) Date of Patent: Jul. 12, 2016

(54) EXHAUST GAS SAMPLING APPARATUS

(71) Applicant: HORIBA, Ltd., Kyoto (JP)

(72) Inventor: Tatsuki Kumagai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 175 days.

(21) Appl. No.: 14/199,692

(22) Filed: Mar. 6, 2014

(65) Prior Publication Data

US 2014/0251031 A1 Sep. 11, 2014

(30) Foreign Application Priority Data

Mar. 7, 2013 (JP) ................................. 2013-044940

(51) Int. Cl.
*G01N 1/22* (2006.01)

(52) U.S. Cl.
CPC ...... *G01N 1/2252* (2013.01); *G01N 2001/2255* (2013.01)

(58) Field of Classification Search
CPC .................... G01N 1/2252; G01N 2001/2255; G01N 2001/2264; G01N 33/0016; G01N 33/0018
See application file for complete search history.

(56) References Cited

U.S. PATENT DOCUMENTS

| | | | | |
|---|---|---|---|---|
| 3,817,100 A * | 6/1974 | Anderson | .................. | G01F 1/00 73/861.63 |
| 4,596,156 A * | 6/1986 | Shimizu | ............... | G01N 1/2252 137/599.03 |
| 4,823,591 A * | 4/1989 | Lewis | ................... | G01F 25/003 73/1.26 |
| 6,443,021 B2 * | 9/2002 | Hanashiro | ................ | G01N 1/00 73/863.11 |
| 6,505,524 B1 * | 1/2003 | Silvis | ................... | G01N 1/2252 73/863.03 |
| 2001/0003915 A1 * | 6/2001 | Inoue | .................... | G01N 1/2252 73/23.2 |
| 2001/0013245 A1 * | 8/2001 | Hanashiro | ................ | G01F 1/44 73/23.31 |
| 2003/0079555 A1 * | 5/2003 | Dickson | ............... | G01N 1/2252 73/863.02 |
| 2011/0120096 A1 * | 5/2011 | Nakamura | .............. | F01N 11/00 60/276 |
| 2014/0290336 A1 * | 10/2014 | Miyai | .................... | G01N 19/10 73/29.01 |
| 2014/0352404 A1 * | 12/2014 | Kumagai | ............. | G01N 1/2247 73/23.31 |
| 2015/0153254 A1 * | 6/2015 | Silvis | ................... | G01M 15/10 73/864 |

FOREIGN PATENT DOCUMENTS

| | | |
|---|---|---|
| DE | 19604417 C1 | 9/1997 |
| EP | 0971211 A2 | 1/2000 |
| JP | 2001-264223 | 9/2001 |
| WO | 0003224 | 1/2000 |

OTHER PUBLICATIONS

EESR dated May 4, 2015 issued for European patent application No. 14 000 805.3, 7 pgs.

* cited by examiner

*Primary Examiner* — Peter Macchiarolo
*Assistant Examiner* — Natalie Huls
(74) *Attorney, Agent, or Firm* — Brooks Kushman P.C.

(57) ABSTRACT

An embodiment of the invention is one that, in the case where a sampling part is configured to include a plurality of venturis, with suppressing an increase in size of an apparatus and an increase in cost, accurately obtains a diluent gas flow rate in accordance with a diluted exhaust gas flow rate obtained on the basis of a combination among the plurality of venturis, in which the sampling part collecting part of diluted exhaust gas is configured to parallel connect the plurality of venturis that control the flow rate of the diluted exhaust gas, and a flow rate control part provided in a diluent gas sampling flow path is configured to parallel connect a plurality of venturis that control the flow rate of diluent gas to be introduced into a diluent gas analyzing device.

4 Claims, 3 Drawing Sheets

EXHAUST GAS SAMPLING APPARATUS

CROSS-REFERENCE TO RELATED APPLICATION

This application claims priority to JP Application No. 2013-044940, filed Mar. 7, 2013, the disclosure of which is incorporated in its entirety by reference herein.

TECHNICAL FIELD

The present invention relates to an exhaust gas sampling apparatus that dilutes exhaust gas emitted from, for example, an engine with diluent gas such as air to sample the diluted exhaust gas.

BACKGROUND

As this sort of exhaust gas sampling apparatus, as disclosed in JP-A2001-264223, there is one that connects a diluent gas flow path for introducing diluent gas to a main flow path through which exhaust gas introduced from an exhaust gas introduction port flows, and on a downstream side of a connecting points between the paths, samples part of diluted exhaust gas to collect the part in a diluted exhaust gas collecting bag. Also, the exhaust gas sampling apparatus samples part of the diluent gas from the diluent gas flow path to collect the part in a diluent gas collecting bag in order to make a background correction of the concentration of a component in the diluted exhaust gas collected in the diluted exhaust gas collecting bag. Further, the exhaust gas sampling apparatus calculates the concentration of the component in the exhaust gas by subtracting the concentration of the component in the diluent gas in the diluent gas collecting bag from the concentration of the component in the diluted exhaust gas in the diluted exhaust gas collecting bag.

Specifically, this exhaust gas sampling apparatus is configured to provide the main flow path with a sampling venturi to collect the diluted exhaust gas in the diluted exhaust gas collecting bag at a constant flow rate, and provide the diluent gas flow path with a needle valve to collect the diluent gas in the diluent gas collecting bag at a constant flow rate. Further, in order to, within a sampling time for the collection into the diluted exhaust gas collecting bag, make an amount of the diluted exhaust gas collected in the diluted exhaust gas collecting bag and an amount of the diluent gas collected in the diluent gas collecting bag substantially the same, the exhaust gas sampling apparatus is configured to make a critical flow rate of the sampling venturi and a control flow rate of the needle valve substantially the same.

For example, in order to change the sampling flow rate or the like along with a change of a test cycle, or perform other operation, it is considered to provide a plurality of sampling venturis to switch or combine among the sampling venturis. In this case, in order to, within the sampling time, make the diluted exhaust gas amount collected in the diluted exhaust gas collecting bag and the diluent gas amount collected in the diluent gas collecting bag substantially the same, it is possible to parallel provide a plurality of needle valves each having the same control flow rate as a critical flow rate of each of the plurality of sampling venturis. Further, in the case of combining among the plurality of sampling venturis to control a diluted exhaust gas flow rate, it is necessary to combine among the plurality of needle valves to control a diluent gas flow rate.

However, although a needle valve determines a flow rate on the basis of a differential pressure between pressures on upstream and downstream sides of the valve, in the case of combining among the plurality of needle valves for use, a pressure condition is different from that of a single body of the valve, and fluid does not flow at a set flow rate, so that the same flow rate as the diluted exhaust gas flow rate cannot be obtained. For this reason, within the sampling time, the diluted exhaust gas amount collected in the diluted exhaust gas collecting bag and the diluent gas amount collected in the diluent gas collecting bag are different from each other, which give rise to a problem that it is difficult to accurately make the background correction.

Also, it is possible to, for each of a plurality of diluted exhaust flow rates obtained by combining among the plurality of sampling venturis, provide a plurality of needle valves each having the same control flow rate as the diluted exhaust gas flow rate; however, there is a problem that an apparatus is increased in size to increase cost.

SUMMARY

Technical Problem

Therefore, a main object of the present invention is to, in the case where a sampling part for collecting diluted exhaust gas is configured to include a plurality of venturis, while suppressing an increase in size of an apparatus and an increase in cost, accurately obtain a diluent gas flow rate in accordance with each of diluted exhaust gas flow rates obtained by combining among the plurality of venturis.

Solution to Problem

That is, an exhaust gas sampling apparatus according to the present invention is provided with: an exhaust gas introduction port for introducing exhaust gas; a diluent gas introduction port for introducing diluent gas; a main flow path of which one end is connected to the exhaust gas introduction port; a diluent gas flow path of which one end is connected to the diluent gas introduction port and the other end is connected to the main flow path; a sampling part that is provided at a connecting point between the main flow path and the diluent gas flow path or on a downstream side of the connecting point to collect part of diluted exhaust gas that is the exhaust gas diluted with the diluent gas; a diluted exhaust gas sampling flow path of which one end is connected to the sampling part and the other end is connected to a diluted exhaust gas analyzing device; a diluent gas sampling flow path of which one end is connected to the diluent gas flow path and the other end is connected to a diluent gas analyzing device; and a flow rate control part that is provided in the diluent gas sampling flow path to control a flow rate of the diluent gas flowing through the diluent gas sampling flow path, wherein: the sampling part is configured to parallel connect a plurality of venturis that control a flow rate of the diluted exhaust gas to be introduced into the diluted exhaust gas analyzing device; and the flow rate control part is configured to parallel connect a plurality of venturis that control a flow rate of the diluent gas to be introduced into the diluent gas analyzing device.

If so, the sampling part is configured to connect the plurality of venturis in parallel, and therefore by switching or combining among the venturis to sample the diluted exhaust gas, the diluted exhaust gas can be introduced into the diluted exhaust gas analyzing device at any of various sampling flow rates. Further, the flow rate control part provided in the diluent gas flow path is configured to connect the plurality of venturis in parallel, and therefore by switching or combining among the venturis of the flow rate control part in accordance with the diluted exhaust gas flow rate determined by the sampling part, the diluent gas flow rate can be accurately obtained. Note that the flow rate control part is configured with use of the plurality of venturis, so that as compared with the case of using a needle valve to configure the diluent gas flow path, an increase in size can be suppressed, and an increase in cost can also be suppressed.

Desirably, the plurality of venturis constituting the sampling part respectively have mutually different critical flow rates; the plurality of venturis constituting the flow rate control part respectively have mutually different critical flow rates; and a combination among the plurality of venturis constituting the sampling part and a combination among the plurality of venturis constituting the flow rate control part are the same. If so, the diluted exhaust gas flow rate determined by the plurality of venturis of the sampling part and the diluent gas flow rate determined by the plurality of venturis of the flow rate control part can be easily made the same with higher accuracy.

Desirably, in the main flow path, on a downstream side of the sampling part, a constant flow rate control device that makes the flow rate of the diluted exhaust gas flowing through the main flow path constant is provided. If so, the exhaust gas sampling apparatus can be used as a constant volume sampling apparatus.

Desirably, the diluted exhaust gas analyzing device is a diluted exhaust gas collecting bag for collecting the diluted exhaust gas; and the diluent gas analyzing device is a diluent gas collecting bag for collecting the diluent gas. In the exhaust gas sampling apparatus using the diluted exhaust gas collecting bag and the diluent gas collecting bag as described, any of the gas collecting bags can be prevented from being broken, and substantially the same amount of gas can be collected in each of the gas collecting bags, so that effects of the present invention are made further noticeable.

Advantageous Effects of Invention

According to the present invention configured as described, the flow rate control part provided in the diluent gas sampling flow path is configured to include the plurality of venturis, so that in the case where the sampling part for collecting the diluted exhaust gas is configured to include the plurality of venturis, the diluent gas flow rate can be accurately obtained in accordance with the diluted exhaust gas flow rate obtained by the combination among the plurality of venturis with the increases in size of the apparatus and cost being suppressed.

DETAILED DESCRIPTION

In the following, an exhaust gas sampling apparatus according to the present invention is described with reference to the drawings.

An exhaust gas sampling apparatus 100 of the present embodiment is one that is used for a gas analyzing system for analyzing a component contained in exhaust gas emitted from, for example, an engine or the like, and of a dilution sampling system that dilutes the exhaust gas with diluent gas such as air (diluent air) several times (e.g., 10 to 20 times) to perform concentration measurement.

Figure 1:
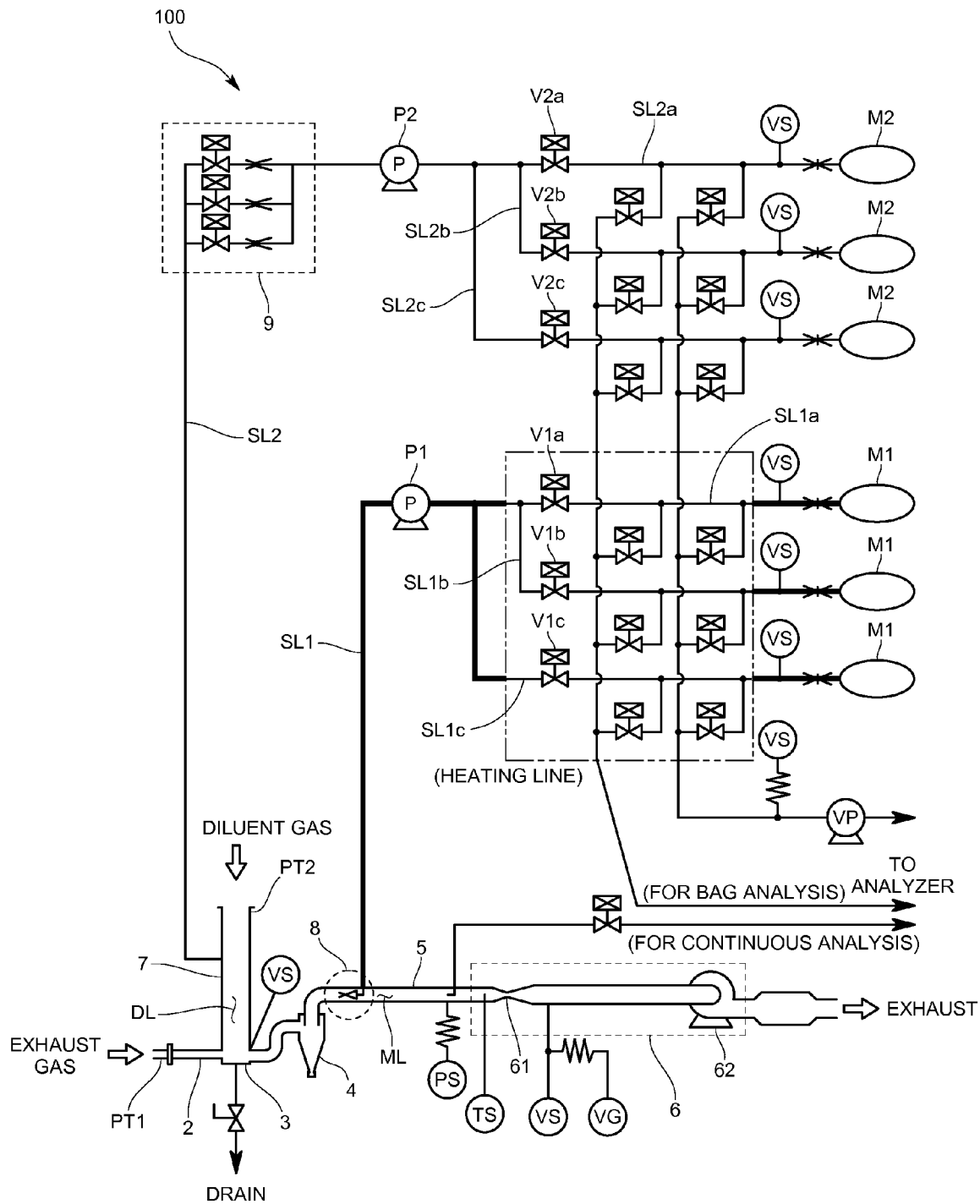
FIG. 1 is a diagram illustrating a configuration of an exhaust gas sampling apparatus of the present embodiment.

Specifically, the exhaust gas sampling apparatus 100 is a constant volume sampling apparatus, and as illustrated in FIG. 1, provided with: a main flow path ML of which one end is connected to an exhaust gas introduction port PT1 for introducing the exhaust gas; and a diluent gas flow path DL of which one end is connected to a diluent gas introduction port PT2 for introducing the diluent gas and the other end is connected to the main flow path ML.

The main flow path ML is configured to include: an exhaust gas introduction pipe 2 of which one end is provided with the exhaust gas introduction port PT1 to introduce the exhaust gas; a mixing part 3 that is connected to the exhaust gas introduction pipe 2; a dust removing cyclone 4 that is connected downstream of the mixing part 3; a sampling pipe 5 that is connected to the cyclone 4; and a constant flow rate control device 6 that is connected to the sampling pipe 5. Also, the diluent gas flow path DL is configured to include a diluent gas introduction pipe 7 of which one end is provided with the diluent gas introduction port PT2. In addition, the diluent gas introduction port PT2 is provided with a filter (not illustrated) for removing impurities in the air.

The mixing part 3 is one that is connected with the diluent gas introduction pipe 7 constituting the diluent gas flow path DL and the exhaust gas introduction pipe 2, and also referred to as, for example, a mixing tee.

Further, the sampling pipe 5 is one that is provided with: an after-mentioned sampling part 8 for bag collection; and a sampling part for continuous measurement.

The constant flow rate control device 6 is one that performs flow rate control so as to make a total flow rate of the exhaust gas introduced from the exhaust gas introduction pipe 2 and the diluent gas introduced from the diluent gas introduction pipe 7 constant, and configured to include: a main venturi 61 that is formed of a critical flow venturi (CFV) connected downstream of the sampling pipe 5; and a suction pump 62 that is connected downstream of the main venturi 61, such as a blower. The suction pump 62 makes a differential pressure between pressures on upstream and downstream sides of the main venturi 61 equal to or more than a required value, and thereby the total flow rate is made constant. In addition, diluted exhaust gas sucked by the suction pump 62 is discharged outside.

Also, the exhaust gas sampling apparatus 100 of the present embodiment is provided with: the sampling part 8 that is provided at a connecting point between the main flow path ML and the diluent gas flow path DL or on a downstream side of the connecting point, and collects part of the diluted exhaust gas that is the exhaust gas diluted with the diluent gas; a diluted exhaust gas sampling flow path SL1 of which one end is connected to the sampling part 8 and the other end is connected to a diluted exhaust gas analyzing device M1 (e.g., a diluted exhaust gas collecting bag); a diluent gas sampling flow path SL2 of which one end is connected to the diluent gas flow path DL and the other end is connected to a diluent gas analyzing device M2; and a flow rate control part 9 that is provided in the diluent gas sampling flow path SL2 and controls a flow rate of the diluent gas flowing through the diluent gas sampling flow path SL2. Note that in the present embodiment, the diluted exhaust gas analyzing device M1 is the diluted exhaust gas collecting bag, and the diluent gas analyzing device M2 is a diluent gas collecting bag.

Figure 2:
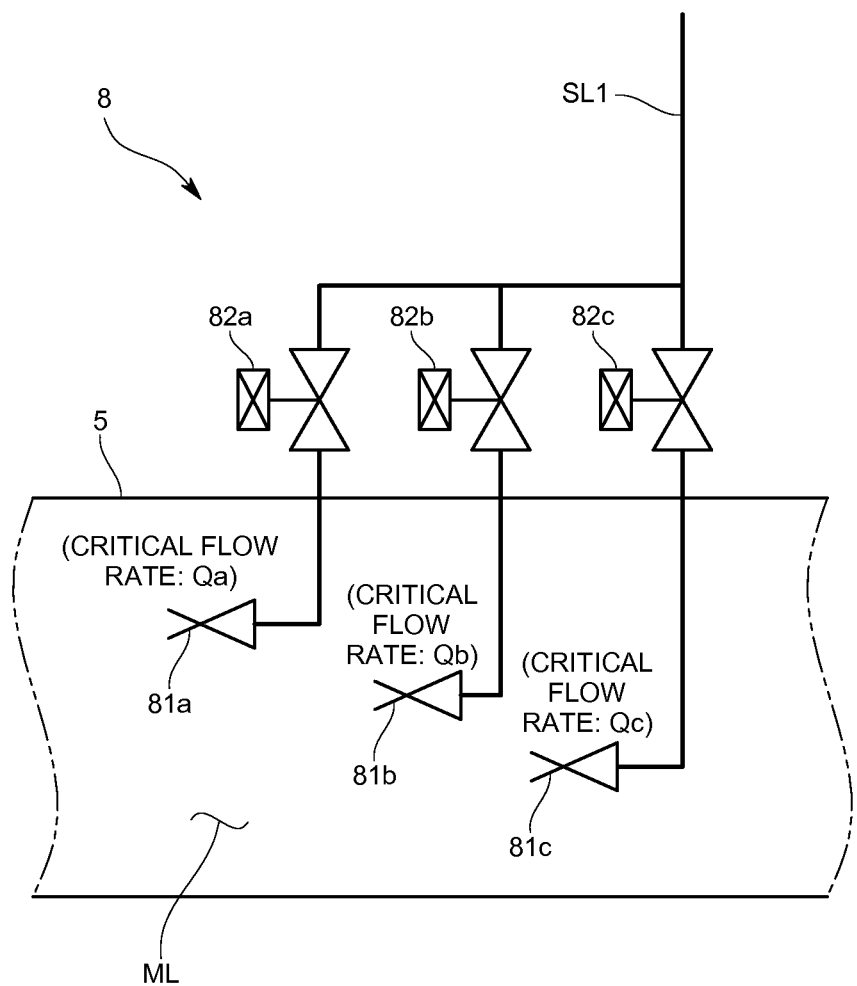
FIG. 2 is a schematic diagram illustrating a specific configuration of a sampling part in the same embodiment.

The sampling part 8 is one that performs proportional sampling of the diluted exhaust gas at a constant flow rate from the main flow path ML in which the total flow rate is made constant by the constant flow rate control device 6, and as illustrated in FIG. 2, configured to parallel connect a plurality of (three in FIG. 2) venturis 81*a* to 81*c* for controlling a flow rate of the diluted exhaust gas to be introduced into the diluted exhaust gas collecting bag M1. Specifically, in the sampling part 8, the venturis 81*a* to 81*c* respectively having mutually different critical flow rates are connected in parallel, and on upstream or downstream sides (in the present embodiment, on the downstream sides) of the respective venturis 81*a* to 81*c*, on/off valves 82*a* to 82*c* are provided. In addition, the on/off valves 82*a* to 82*c* are solenoid valves controlled by an after-mentioned control device (not illustrated). On downstream sides of the on/off valves 82*a* to 82*c*, respective flow paths meet together, and are communicatively connected to the diluted exhaust gas sampling flow path SL1.

Note that, regarding the venturis 81*a* to 81*c* in the sampling part 8, in the case where regardless of an upstream side pressure, a pressure difference equal to or more than a required value is generated between the upstream side pressure and a downstream side pressure, a flow rate of the gas passing through each of the venturis 81*a* to 81*c* becomes constant at a corresponding one of the critical flow rates; however, in practice, the flow rate is calculated from a detected pressure (P) and a detected temperature (T) respectively detected by a pressure sensor PS and a temperature sensor TS that are provided on the upstream side of the main venturi 61, and a specific venturi coefficient C that is preliminarily examined in an atmospheric pressure environment ($Q=C \cdot P \cdot T^{-1/2}$). Further, by integrating the calculated gas flow rate, sampling of the diluted exhaust gas is ended before an integrated value exceeds the volume of each of the diluted exhaust gas collecting bags M1.

The diluted exhaust gas sampling flow path SL1 is, at the one end thereof, connected to the sampling part 8, and on a downstream side thereof, branches into a plurality of branched paths, and the other ends of the respective sampling branched paths SL1*a* to SL1*c* are connected to diluted exhaust gas collecting bags M1. The respective sampling branched paths SL1*a* to SL1*c* are provided with on/off valves V1*a* to V1*c* for switching among the diluted exhaust gas collecting bags M1 to perform the collection. Also, on an upstream side of a branching point in the diluted exhaust gas sampling flow path SL1, a suction pump P1 for making the gas flow rate flowing through each of the venturis 81*a* to 81*c* of the sampling part 8 equal to a corresponding one of the critical flow rates is provided. In addition, between the suction pump P1 and the branching point, a drain separator and a flowmeter (any of which is not illustrated) are provided. Further, the diluted exhaust gas sampling flow path SL1 is heated by an external heater or the like, and configured to prevent a component contained in the diluted exhaust gas, such as water, from being condensed.

The diluent gas sampling flow path SL2 is, at the one end thereof, connected to the diluent gas introduction pipe 7 constituting the diluent gas flow path DL, and on a downstream side thereof, branches into a plurality of branched paths, and the other ends of the respective sampling branched paths SL2*a* to SL2*c* are connected to diluent gas collecting bags M2. The respective sampling branched paths SL2*a* to SL2*c* are provided with on/off valves V2*a* to V2*c* for switching among the diluent gas collecting bags M2 to perform the collection. Also, on an upstream side of a branching point in the diluent gas sampling flow path SL2, a suction pump P2 for making a gas flow rate flowing through each of venturis 91*a* to 91*c* of the after-mentioned flow rate control part 9 equal to a critical flow rate is provided. In addition, between the suction pump P2 and the branching point, a drain separator and a flowmeter (any of which is not illustrated) are provided.

Figure 3:
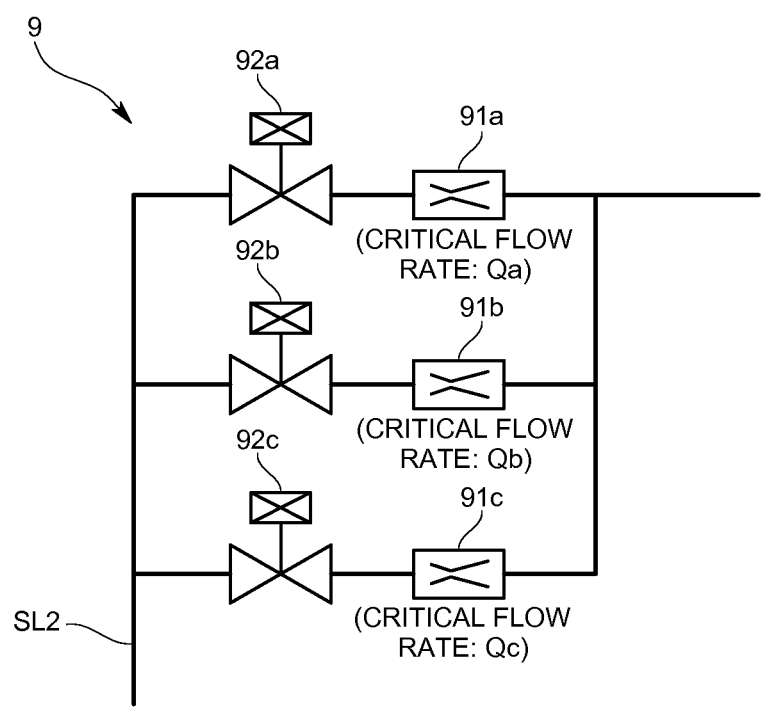
FIG. 3 is a schematic diagram illustrating a specific configuration of a flow rate control part in the same embodiment.

The flow rate control part 9 is, as illustrated in FIG. 3, configured to parallel connect the plurality of (three in FIG. 3) venturis 91*a* to 91*c* that are provided in the diluent gas sampling flow path SL2 to control a flow rate of the diluent gas to be introduced into any of the diluent gas collecting bags M2. Specifically, in the flow rate control part 9, the venturis 91*a* to 91*c* respectively having mutually different critical flow rates are connected in parallel, and on upstream or downstream sides (in the present embodiment, on the upstream sides) of the respective venturis 91*a* to 91*c*, on/off valves 92*a* to 92*c* are provided. In addition, the on/off valves 92*a* to 92*c* are solenoid valves controlled by the after-mentioned control device (not illustrated).

Note that, regarding the venturis 91*a* to 91*c* of the flow rate control part 9, in the case where regardless of an upstream side pressure, a pressure difference equal to or more than a required value is generated between the upstream side pressure and a downstream side pressure, a flow rate of the gas passing through each of the venturis 91*a* to 91*c* becomes constant at a corresponding one of the critical flow rates; however, in practice, the flow rate is calculated from a predetermined reference pressure ($P_0$) and reference temperature ($T_0$), and a specific venturi coefficient C that is preliminarily examined in an atmospheric pressure environment ($Q=C \cdot P_0 \cdot T_0^{-1/2}$). Further, by integrating the calculated gas flow rate, sampling of the diluent gas is ended before an integrated value exceeds the volume of each of the diluent gas collecting bags M2, or when the sampling by the sampling part 8 is ended, simultaneously ended.

Further, the present embodiment is configured such that the respective critical flow rates of the three venturis 91*a* to 91*c* constituting the flow rate control part 9 and the respective critical flow rates of the three venturis 81*a* to 81*c* constituting the sampling part 8 are almost the same. That is, a combination of the three venturis 81*a* to 81*c* constituting the sampling part 8 and a combination of the three venturis 91*a* to 91*c* constituting the flow rate control part 9 are the same. For example, the venturi 81*a* and the venturi 91*a* are the same (critical flow rate: Qa); the venturi 81*b* and the venturi 91*b* are the same (critical flow rate: Qb); and the venturi 81*c* and the venturi 91*c* are the same (critical flow rate: Qc).

Next, operation of the control device that controls the sampling part 8 and flow rate control part 9 configured as described is briefly described.

The control device performs on/off control of the on/off valves 82*a* to 82*c* of the sampling part 8 such that, among the three venturis 81*a* to 81*c* constituting the sampling part 8, on the basis of a setting flow rate preset for each of the diluted exhaust gas collecting bags M1, a combined flow rate among the venturis 81*a* to 81*c* to collect the diluted exhaust gas is made equal to the setting flow rate. As illustrated in FIG. 2, in the case of the sampling part 8 having the three venturis 81*a* to 81*c*, seven different flow rates can be set in total.

Also, the control device performs on/off control of the on/off valves 92*a* to 92*c* of the flow rate control part 9 so as to meet the setting flow rate or the combined flow rate among the venturis 81*a* to 81*c* of the sampling part 8. Note that the flow rate control part 9 of the present embodiment has the same configuration as that of the sampling part 8, and therefore the on/off control of the on/off valves 92*a* to 92*c* are performs such that the on/off valves 92*a* to 92*c* have the same combination as the on/off combination among the on/off valves 82*a* to 82*c* of the sampling part 8.

The control device controls the sampling part 8 and flow rate control part 9 as described, and thereby within the same sampling time, an amount of the diluted exhaust gas introduced into each of the diluted exhaust gas collecting bags M1 and an amount of the diluent gas introduced into each of the diluent gas collecting bags M2 are made the same.

According to the exhaust gas sampling apparatus 100 according to the present embodiment configured as described, the sampling part 8 is configured to connect the plurality of venturis 81a to 81c in parallel, and therefore by switching or combining among the venturis 81a to 81c to sample the diluted exhaust gas, the diluted exhaust gas can be introduced into each of the diluted exhaust gas collecting bags M1 at any of the various sampling flow rates.

Also, the flow rate control part 9 provided in the diluent gas flow path DL is configured to connect the plurality of venturis 91a to 91c in parallel, and therefore by switching or combining among the venturis 91a to 91c of the flow rate control part 9 in accordance with a diluted exhaust gas flow rate determined by the sampling part 8, a diluent gas flow rate can be accurately obtained.

Note that the flow rate control part 9 is configured with use of the plurality of venturis 91a to 91c, so that as compared with the case of using a needle valve to configure the diluent gas flow path DL, an increase in size can be suppressed and an increase in cost can also be suppressed.

In addition, in the case where the flow rate control part 9 is configured to connect a plurality of needle valves in parallel, a reduction in pressure on upstream sides of the valves influences a flow rate; however, in the case of the venturis 91a to 91c of the present embodiment, by reducing the downstream side pressure with the suction pump P2, regardless of the upstream side pressure, to make the differential pressure between pressures on upstream and downstream sides of the venturis 91a to 91c equal to or more than the required value, a constant flow rate can be obtained to accurately obtain a diluent gas flow rate.

Note that the present invention is not limited to the above-described embodiment.

For example, in the above-described embodiment, each of the sampling part 8 and the flow rate control part 9 is configured with use of the venturis respectively having the mutually different critical flow rates; however, it may be configured with use of venturis having the same critical flow rate.

Also, in the above-described embodiment, the combination among the plurality of venturis constituting the sampling part 8 and the combination among the plurality of venturis constituting the flow rate control part 9 are the same; however, the combinations may be different. Also, the number of venturis constituting the sampling part 8 and the number of venturis constituting the flow rate control part 9 may be different from each other.

Further, in the case of using the exhaust gas sampling apparatus of the above-described embodiment in a low pressure chamber of which a pressure is lower than atmospheric pressure, a flow rate error occurs in the venturis 91a to 91c constituting the flow rate control part 9. This is because the venturis 91a to 91c constituting the flow rate control part 9 are regulated to achieve a desired gas flow rate in atmospheric pressure, and to calculate the gas flow rate, the predetermined reference temperature and reference pressure are used. For this reason, the present invention may be configured to, in order to calculate the flow rate of the gas flowing through the venturis 91a to 91c of the flow rate control part 9, use the detected pressure and the detected temperature respectively detected by the pressure sensor PS and the temperature sensor TS provided in the sampling pipe 5 to perform the calculation. If so, as compared with the case of using the reference pressure and the reference temperature, the flow rate of the gas flowing through the venturis 91a to 91c of the flow rate control part 9 can be accurately calculated to prevent each of the diluent gas collecting bags M2 from being broken.

Further, in the above-described embodiment, the diluted exhaust gas analyzing device and the diluent gas analyzing device are the gas collecting bags, respectively, however, besides, the analyzing devices may be PM filters or the like for collecting PM contained in the gases.

In addition, the exhaust gas sampling apparatus of the above-described embodiment is one that dilutes the total amount of the exhaust gas; however, the exhaust gas sampling apparatus may be one that partially dilutes the exhaust gas. That is, the exhaust gas sampling apparatus may be one adapted such that the exhaust gas introduction port PT1 collects part of the exhaust gas to introduce the part into the main flow path ML.

Besides, it should be appreciated that the present invention is not limited to any of the above-described embodiments, but can be variously modified without departing from the scope thereof.

REFERENCE SIGNS LIST

100: Exhaust gas sampling apparatus
PT1: Exhaust gas introduction port
PT2: Diluent gas introduction port
ML: Main flow path
DL: Diluent gas flow path
8: Sampling part
81a to 81c: Plurality of venturis
SL1: Diluted exhaust gas sampling flow path
M1: Diluted exhaust gas collecting bag (diluted exhaust gas analyzing device)
SL2: Diluent gas sampling flow path
M2: Diluent gas collecting bag (diluent gas analyzing device)
9: Flow rate control part
91a to 91c: Plurality of venturis

What is claimed is:

1. An exhaust gas sampling apparatus comprising:
an exhaust gas introduction port for introducing exhaust gas;
a diluent gas introduction port for introducing diluent gas;
a main flow path of which one end is connected to the exhaust gas introduction port;
a diluent gas flow path of which one end is connected to the diluent gas introduction port and the other end is connected to the main flow path;
a sampling part that is provided at a connecting point between the main flow path and the diluent gas flow path or on a downstream side of the connecting point to collect part of diluted exhaust gas that is the exhaust gas diluted with the diluent gas;
a diluted exhaust gas sampling flow path of which one end is connected to the sampling part and the other end is connected to a diluted exhaust gas analyzing device;
a diluent gas sampling flow path of which one end is connected to the diluent gas flow path and the other end is connected to a diluent gas analyzing device; and
a flow rate control part that is provided in the diluent gas sampling flow path to control a flow rate of the diluent gas flowing through the diluent gas sampling flow path, wherein:
the sampling part includes a plurality of venturis connected in parallel that controls a flow rate of the diluted exhaust gas to be introduced into the diluted exhaust gas analyzing device, the flow rate control part includes a plurality of venturis connected in parallel that controls a flow rate of the diluent gas to be introduced into the diluent gas analyzing device, and corresponding members of the plurality of venturis that controls the flow rate of the diluted exhaust gas and the plurality of venturis that controls the flow rate of the diluent gas have a same critical flow rate.

2. The exhaust gas sampling apparatus according to claim 1, wherein:

the plurality of venturis that controls the flow rate of the diluted exhaust gas respectively has mutually different critical flow rates, and the plurality of venturis that controls the flow rate of the diluent gas respectively has mutually different critical flow rates.

3. The exhaust gas sampling apparatus according to claim 1 further comprising a constant flow rate control device, that makes the flow rate of the diluted exhaust gas flowing through the main flow path constant, provided in the main flow path on a downstream side of the sampling part.

4. The exhaust gas sampling apparatus according to claim 1, wherein:

the diluted exhaust gas analyzing device is a diluted exhaust gas collecting bag for collecting the diluted exhaust gas, and the diluent gas analyzing device is a diluent gas collecting bag for collecting the diluent gas.

* * * * *